United States Patent
Wang et al.

(10) Patent No.: US 10,886,565 B2
(45) Date of Patent: Jan. 5, 2021

(54) ELECTROLYTE AND ELECTROCHEMICAL ENERGY STORAGE DEVICE

(71) Applicant: CONTEMPORARY AMPEREX TECHNOLOGY CO., LIMITED, Ningde (CN)

(72) Inventors: Xiaomei Wang, Ningde (CN); Chenghua Fu, Ningde (CN); Changlong Han, Ningde (CN)

(73) Assignee: CONTEMPORARY AMPEREX TECHNOLOGY CO., LIMITED, Ningde (CN)

( * ) Notice: Subject to any disclaimer, the term of this patent is extended or adjusted under 35 U.S.C. 154(b) by 43 days.

(21) Appl. No.: 16/026,990

(22) Filed: Jul. 3, 2018

(65) Prior Publication Data
US 2019/0036168 A1 Jan. 31, 2019

(30) Foreign Application Priority Data
Jul. 27, 2017 (CN) .......................... 2017 1 0624392

(51) Int. Cl.
| | | |
|---|---|---|
| *H01M 10/0567* | (2010.01) | |
| *H01M 10/0568* | (2010.01) | |
| *H01G 11/62* | (2013.01) | |
| *H01G 11/64* | (2013.01) | |
| *C07D 207/06* | (2006.01) | |
| *C07F 9/6574* | (2006.01) | |
| *C07D 307/64* | (2006.01) | |
| *C07D 213/71* | (2006.01) | |
| *C07D 295/15* | (2006.01) | |
| *C07F 5/04* | (2006.01) | |
| *C07D 295/24* | (2006.01) | |
| *H01M 10/052* | (2010.01) | |
| *H01G 11/56* | (2013.01) | |
| *H01M 10/0525* | (2010.01) | |

(52) U.S. Cl.
CPC ...... *H01M 10/0567* (2013.01); *C07D 207/06* (2013.01); *C07D 213/71* (2013.01); *C07D 295/15* (2013.01); *C07D 295/24* (2013.01); *C07D 307/64* (2013.01); *C07F 5/04* (2013.01); *C07F 9/65742* (2013.01); *C07F 9/65748* (2013.01); *H01G 11/56* (2013.01); *H01G 11/62* (2013.01); *H01G 11/64* (2013.01); *H01M 10/052* (2013.01); *H01M 10/0568* (2013.01); *H01M 10/0525* (2013.01); *H01M 2300/0025* (2013.01)

(58) Field of Classification Search
None
See application file for complete search history.

(56) References Cited

U.S. PATENT DOCUMENTS

| | | | |
|---|---|---|---|
| 2006/0035144 A1* | 2/2006 | Shimizu | H01M 10/0567 429/188 |
| 2014/0193707 A1* | 7/2014 | Schmidt | C07F 5/022 429/201 |
| 2014/0295288 A1 | 10/2014 | Ding | |
| 2015/0349381 A1* | 12/2015 | Hwang | H01M 10/0567 429/188 |

FOREIGN PATENT DOCUMENTS

| | | | |
|---|---|---|---|
| CN | 104852087 A | | 8/2015 |
| CN | 105186036 A | | 12/2015 |
| CN | 105845981 A | * | 8/2016 |
| CN | 105845981 A | | 8/2016 |
| CN | 105932332 A | | 9/2016 |
| CN | 106099184 A | | 11/2016 |
| DE | 112012004415 T5 | | 8/2014 |
| EP | 2120279 A1 | | 11/2009 |
| WO | WO 2013/026854 A1 | | 2/2013 |
| WO | WO 2015/150390 A1 | | 10/2015 |

OTHER PUBLICATIONS

Contemporary Amperex Technology Co.,Limited, Extended European Search Report, EP18185401-9, dated Dec. 11, 2018, 10 pgs.
Contemporary Amperex Technology Co., Limited, First Office Action, CN 201710624392.2, dated Feb. 2, 2020, 9 pgs.

* cited by examiner

*Primary Examiner* — Scott J. Chmielecki
(74) *Attorney, Agent, or Firm* — Morgan, Lewis & Bockius LLP

(57) ABSTRACT

The present disclosure provides an electrolyte and an electrochemical energy storage device, the electrolyte comprises an electrolyte salt and an additive. The additive comprises a sulfonic ester cyclic quaternary ammonium salt and a multinitrile compound. The sulfonic ester cyclic quaternary ammonium salt and the multinitrile compound can form a dense and uniform passive film with high ionic conductivity on a surface of each of the positive electrode film and the negative electrode film, so as to prevent continuous oxidation and reduction reaction from occurring between the electrolyte and the positive electrode film and the negative electrode film and make the electrochemical energy storage device has excellent high temperature cycle performance and high temperature storage performance.

6 Claims, No Drawings

US 10,886,565 B2

ELECTROLYTE AND ELECTROCHEMICAL ENERGY STORAGE DEVICE

CROSS-REFERENCE TO RELATED APPLICATIONS

The present application claims priority to Chinese patent application No. CN201710624392.2, filed on Jul. 27, 2017, which is incorporated herein by reference in its entirety.

FIELD OF THE PRESENT DISCLOSURE

The present disclosure relates to the field of energy storage device, and more specifically relates to an electrolyte and an electrochemical energy storage device.

BACKGROUND OF THE PRESENT DISCLOSURE

With the increasing depletion of fossil fuels and increasing pressure on environmental pollution, automotive industry urgently needs a new type energy resource to provide driving force for automobiles, and lithium-ion battery is talent showing itself due to its high energy density, no memory effect and high operating voltage, which makes the lithium-ion battery become a first choice for a power supply of the new energy vehicles at present. However, with the expansion of the market demand for electronic products and development of power device and energy storage device, people's demand for the lithium-ion battery is continuously increasing, developing high energy density and fast charge-discharge lithium-ion battery becomes an urgent matter. At present, an effective method is to increase voltage and press density of an electrode active material and select appropriate electrolyte.

At present, an electrolyte widely used in the lithium-ion battery comprises lithium hexafluorophosphate ($LiPF_6$) as an electrolyte salt and a mixture of cyclic carbonate ester and chain carbonate ester as an organic solvent, however the above electrolyte has many disadvantages, particularly under high voltage, high temperature storage performance of the lithium-ion battery is poor. The electrolyte, as an important part of the lithium-ion battery, has a significant influence on electrochemical performance of the lithium-ion battery. The high temperature storage performance and the high temperature cycle performance of the lithium-ion battery can be improved to a certain extent by improving the composition of the electrolyte.

SUMMARY OF THE PRESENT DISCLOSURE

In view of the problem existing in the background, an object of the present disclosure is to provide an electrolyte and an electrochemical energy storage device, the electrolyte comprises an additive, the additive comprises a sulfonic ester cyclic quaternary ammonium salt and a multinitrile compound, the sulfonic ester cyclic quaternary ammonium salt and the multinitrile compound can form a dense and uniform passive film with high ionic conductivity on a surface of each of the positive electrode film and the negative electrode film, so as to prevent continuous oxidation and reduction reaction from occurring between the electrolyte and the positive electrode film and the negative electrode film and make the electrochemical energy storage device have excellent high temperature cycle performance and high temperature storage performance.

In order to achieve the above object, in a first aspect of the present disclosure, the present disclosure provides an electrolyte which comprises an electrolyte salt and an additive. The additive comprises a sulfonic ester cyclic quaternary ammonium salt and a multinitrile compound.

In a second aspect of the present disclosure, the present disclosure provides an electrochemical energy storage device which comprises the electrolyte according to the first aspect of the present disclosure.

Compared to the technology in the background, the present disclosure has the following beneficial effects: the additive of the electrolyte of the present disclosure comprises the sulfonic ester cyclic quaternary ammonium salt and the multinitrile compound, the sulfonic ester cyclic quaternary ammonium salt and the multinitrile compound can form a dense and uniform passive film with high ionic conductivity on the surface of each of the positive electrode film and the negative electrode film, so as to prevent continuous oxidation and reduction reaction from occurring between the electrolyte and the positive electrode film and the negative electrode film and make the electrochemical energy storage device have excellent high temperature cycle performance and high temperature storage performance.

DETAILED DESCRIPTION

Hereinafter an electrolyte and an electrochemical energy storage device according to the present disclosure will be described in detail.

Firstly, an electrolyte according to a first aspect of the present disclosure will be described.

An electrolyte according to a first aspect of the present disclosure comprises an electrolyte salt and an additive. The additive comprises a sulfonic ester cyclic quaternary ammonium salt and a multinitrile compound.

In the electrolyte according to the first aspect of the present disclosure, the sulfonic ester cyclic quaternary ammonium salt is one or more selected from a group consisting of compound represented by formula 1; in the formula 1, Ru is one selected from a group consisting of —CN, C1~C12 alkyl group, C1~C12 alkyl group substituted with a substituent, C2~C12 alkenyl group, C2~C12 alkenyl group substituted with the substituent, C2~C12 alkynyl group, C2~C12 alkynyl group substituted with the substituent, C1~C12 alkoxy group, C1~C12 alkoxy group substituted with the substituent, C1~C12 acyloxy group and C1~C12 acyloxy group substituted with the substituent; $R_{12}$ is one selected from a group consisting of C1~C12 alkylene group, C1~C12 alkylene group substituted with the substituent, C2~C12 alkenylene group, C2~C12 alkenylene group substituted with the substituent, C2~C12 alkynylene group, C2~C12 alkynylene group substituted with the substituent, C1~C12 alkanoyl group and C1~C12 alkanoyl group substituted with the substituent; $R_{13}$ is one selected from a group consisting of C1~C12 alkyl group, C1~C12 alkyl group substituted with the substituent, C2~C12 alkenyl group, C2~C12 alkenyl group substituted with the substituent, C2~C12 alkynyl group, C2~C12 alkynyl group substituted with the substituent, C1~C12 alkoxy group, C1~C12 alkoxy group substituted with the substituent, C1~C12 acyloxy group, C1~C12 acyloxy group substituted with the substituent, C6~C22 aryl group, C6~C22 aryl group substituted with the substituent, C5~C22 heteroaryl group and C5~C22 heteroaryl group substituted with the substituent; $R_{14}$ is one selected from a group consisting of C1~C3 alkylene group and C1~C3 alkylene group substituted with the substituent.

The substituent is one or more selected from a group consisting of —CN and halogen atom.

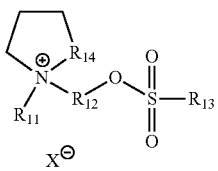

formula 1 in the formula 1, $X^{\ominus}$ represents an anion, $X^{\ominus}$ is one selected from a group consisting of $F^-$, $NO_3^-$, $SO_4^{2-}$, $PF_6^-$, $PF_4^-$, $AsF_6^-$, $(FSO_2)_2N^-$,

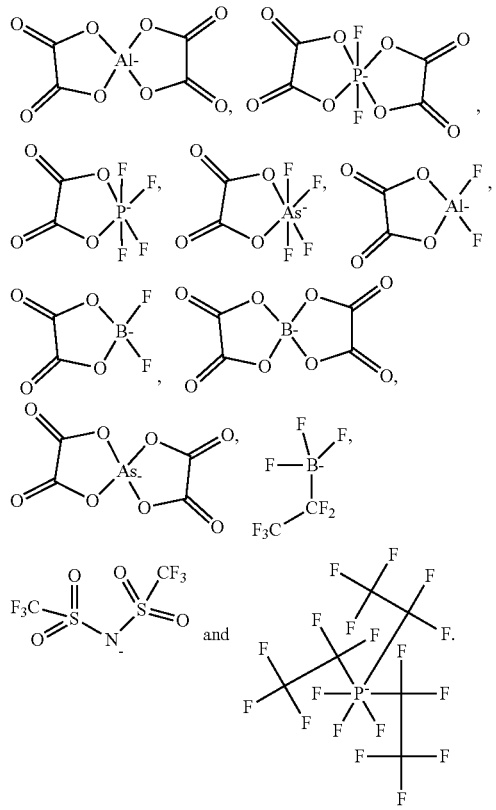

and

In the electrolyte according to the first aspect of the present disclosure, the multinitrile compound is one or more selected from a group consisting of a dinitrile compound, a trinitrile compound and a tetranitrile compound. Specifically, the dinitrile compound may be one or more selected from a group consisting of compound represented by formula 2, in the formula 2, $R_{21}$ is one selected from a group consisting of C1~C20 alkylene group, halogenated C1~C20 alkylene group, C1~C20 alkyleneoxy group, halogenated C1~C20 alkyleneoxy group, C2~C20 alkenylene group, halogenated C2~C20 alkenylene group, C2~C20 alkenyleneoxy group and halogenated C2~C20 alkenyleneoxy group; the trinitrile compound may be one or more selected from a group consisting of compound represented by formula 3, in the formula 3, $R_{31}$, $R_{32}$ and $R_{33}$ each independently are one selected from a group consisting of C0~C20 alkylene group, halogenated C0~C20 alkylene group, C1~C20 alkyleneoxy group, halogenated C1~C20 alkyleneoxy group, C2~C20 alkenylene group, halogenated C2~C20 alkenylene group, C2~C20 alkenyleneoxy group and halogenated C2~C20 alkenyleneoxy group; the tetranitrile compound may be one or more selected from a group consisting of compound represented by formula 4, in the formula 4, $R_{41}$, $R_{42}$, $R_{43}$ and $R_{44}$ each independently are one selected from a group consisting of C0~C20 alkylene group, halogenated C0~C20 alkylene group, C1~C20 alkyleneoxy group, halogenated C1~C20 alkyleneoxy group, C2~C20 alkenylene group, halogenated C2~C20 alkenylene group, C2~C20 alkenyleneoxy group and halogenated C2~C20 alkenyleneoxy group. Here, halogen atom in above "halogenated" may be one or more selected from a group consisting of F, Cl, Br and I.

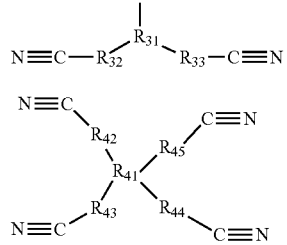

formula 2 formula 3 formula 4

In the electrolyte according to the first aspect of the present disclosure, the electrolyte is a liquid electrolyte, a solid polymer electrolyte or a gel polymer electrolyte.

In the electrolyte according to the first aspect of the present disclosure, a complex reaction will occur between the multinitrile compound and metal ions of a positive electrode active material, a dense and uniform passive film can form on the surface of the positive electrode film, which can effectively prevent metal ions of the positive electrode active material from dissolving out and reduce side reactions of the electrolyte under high temperature on an interface of the positive electrode plate, so as to improve high temperature storage performance and high temperature cycle performance of the electrochemical energy storage device, however due to strong electron attracting ability of a nitrile group, the multinitrile compound can easily get electrons at the negative electrode film to generate a reduction reaction, its reduction products are unstable and will be deposited on the negative electrode film, so as to influence high temperature storage performance and high temperature cycle performance of the electrochemical energy storage device; however due to special structure of a cationic group of the sulfonic ester cyclic quaternary ammonium salt (that is the cationic group of the sulfonic ester cyclic quaternary ammonium salt is composed of a cyclic quaternary ammonium head with unit positive charge and a functional sulfonic ester tail connected through an organic carbon chain therebetween), when reduction potential is 1.5V, the cyclic quaternary ammonium head with unit positive charge can bring whole cationic group proactively close to the negative electrode film and can preferentially be reduction-decomposed to break bond and release the functional sulfonic ester tail, which can form a passive film composed of alkyl sulfonic metal salt ($RSO_3X$) and the like on the surface of the negative electrode film, due to high intrinsic ionic conductivity and high thermal stability of the alkyl sulfonic metal salt, the passive film thus formed on the surface of the negative electrode film has dense and uniform internal structure, low impedance and excellent high temperature performance, which can inhibit occurrence of reduction reaction of the multinitrile compound on the negative electrode film, so as to improve high temperature cycle performance and high temperature storage performance of the electrochemical energy storage device.

In the electrolyte according to the first aspect of the present disclosure, in the formula 1, preferably, $R_{11}$ is one selected from a group consisting of C1~C6 alkyl group, C1~C6 alkyl group substituted with the substituent, halogenated C1~C6 alkyl group and halogenated C1~C6 alkyl group substituted with the substituent, $R_{12}$ is one selected from a group consisting of C1~C12 alkylene group and C1~C12 alkylene group substituted with the substituent, $R_{13}$ is one selected from a group consisting of C1~C6 alkyl group, C1~C6 alkyl group substituted with the substituent, halogenated C1~C6 alkyl group and halogenated C1~C6 alkyl group substituted with the substituent, $R_{14}$ is one selected from a group consisting of C1~C2 alkylene group and C1~C2 alkylene group substituted with the substituent group.

In the electrolyte according to the first aspect of the present disclosure, the cationic group of the sulfonic ester cyclic quaternary ammonium salt is one selected from a group consisting of

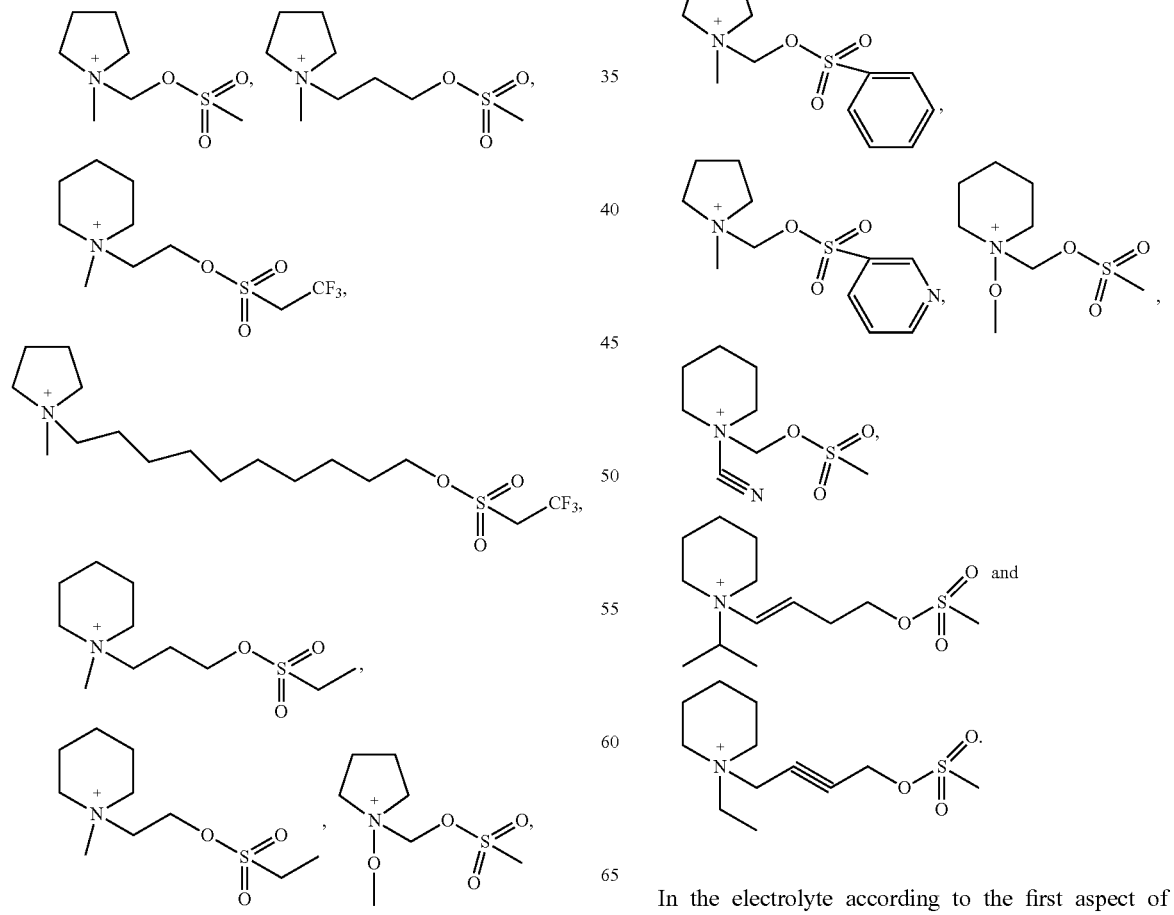

In the electrolyte according to the first aspect of the present disclosure, the sulfonic ester cyclic quaternary ammonium salt is one or more selected from a group consisting of following compound; but the present disclosure is not limited to this;

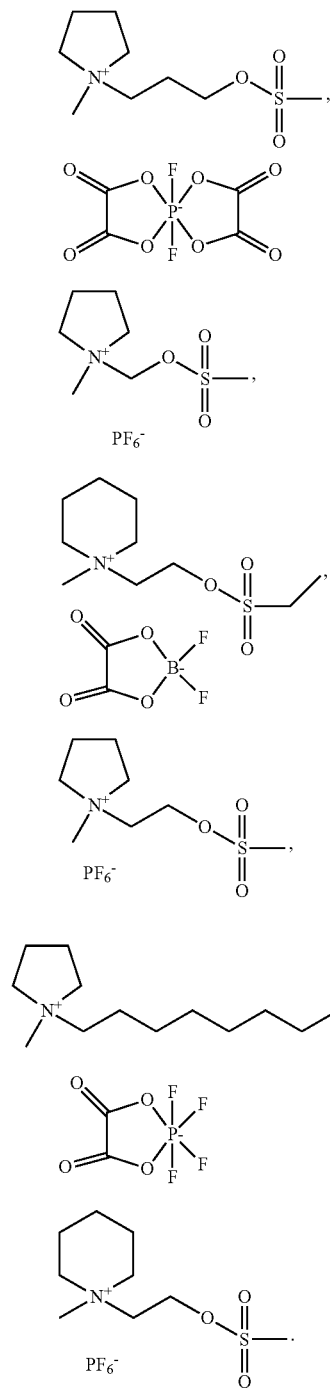

compound 1 compound 2 compound 3 compound 4 compound 5 compound 6

In the electrolyte according to the first aspect of the present disclosure, in the formula 2, preferably, $R_{21}$ is one selected from a group consisting of C1~C10 alkylene group, halogenated C1~C10 alkylene group, C1~C10 alkyleneoxy group, halogenated C1~C10 alkyleneoxy group, C2~C10 alkenylene group, halogenated C2~C10 alkenylene group, C2~C10 alkenyleneoxy group and halogenated C2~C10 alkenyleneoxy group. Here, halogen atom in the above "halogenated" may be one or more selected from a group consisting of F, Cl and Br, the number of oxygen atom of each of the alkyleneoxy group, the halogenated alkyleneoxy group, the alkenyleneoxy group and the halogenated alkenyleneoxy group may be 1, 2 or more.

In the electrolyte according to the first aspect of the present disclosure, specifically, the dinitrile compound may be one or more selected from a group consisting of malononitrile, succinonitrile, 2-methylsuccinonitrile, tetramethylsuccinonitrile, glutaronitrile, 2-methylglutaronitrile, 1,4-dicyanobutane, fumaronitrile, 2-methyleneglutaronitrile, 3,5-dioxa-heptanedinitrile, ethylene glycol bis(2-cyanoethyl)ether, diethylene glycol bis(2-cyanoethyl)ether, triethylene glycol bis(2-cyanoethyl)ether, tetraethylene glycol bis(2-cyanoethyl)etherr, 1,2-bis(2-cyanoethoxy)ethane, 1,3-bis(2-cyanoethoxy)propane, 1,4-bis(2-cyanoethoxy)butane, 1,5-bis(2-cyanoethoxy)pentane, ethylene glycol bis(4-cyanobutyl)ether, 1,8-octanedinitrile, 1,2-dibromo-2,4-dicyanobutane and ethoxymethylenemalononitrile.

In the electrolyte according to the first aspect of the present disclosure, in the formula 3, preferably, $R_{31}$, $R_{32}$ and $R_{33}$ each independently are one selected from a group consisting of C1~C10 alkylene group, halogenated C1~C10 alkylene group, C1~C10 alkyleneoxy group, halogenated C1~C10 alkyleneoxy group, C2~C10 alkenylene group, halogenated C2~C10 alkenylene group, C2~C10 alkenyleneoxy group and halogenated C2~C10 alkenyleneoxy group. Here, halogen atom in the above "halogenated" may be one or more selected from a group consisting of F, Cl and Br, the number of oxygen atom of each of the alkyleneoxy group, the halogenated alkyleneoxy group, the alkenyleneoxy group and the halogenated alkenyleneoxy group may be 1, 2 or more.

In the electrolyte according to the first aspect of the present disclosure, specifically, the trinitrile compound may be one or more selected from a group consisting of methanetricarbonitrile, ethylene-1,1,2-tricarbonitrile, 1,3,6-hexanetricarbonitrile, 1,2,3-propanetricanrbonitrile and 1,3,5-pentanetricarbonitrile.

In the electrolyte according to the first aspect of the present disclosure, in the formula 4, preferably, $R_{41}$, $R_{42}$, $R_{43}$ and $R_{44}$ each independently are one selected from a group consisting of C1~C10 alkylene group, halogenated C1~C10 alkylene group, C1~C10 alkyleneoxy group, halogenated C1~C10 alkyleneoxy group, C2~C10 alkenylene group, halogenated C2~C10 alkenylene group, C2~C10 alkenyleneoxy group and halogenated C2~C10 alkenyleneoxy group. Here, halogen atom in the above "halogenated" may be one or more selected from a group consisting of F, Cl and Br, the number of oxygen atom of each of the alkyleneoxy group, the halogenated alkyleneoxy group, the alkenyleneoxy group and the halogenated alkenyleneoxy group may be 1, 2 or more.

In the electrolyte according to the first aspect of the present disclosure, specifically, the tetranitrile compound may be one or more selected from a group consisting of tetracyanoethylene, 1,2,2,3-propanetetracarbonitrile, methanetetracarbonitrile, 1,1,3,3-propanetetracarbonitrile and 1,1,2,2-ethanetetracarbonitrile.

In the electrolyte according to the first aspect of the present disclosure, because the liquid electrolyte, the solid polymer electrolyte and the gel polymer electrolyte are similar in action mechanism, only the liquid electrolyte is taken as an example for description in the present disclosure, that is in the following description, the electrolytes all refer to the liquid electrolyte.

In the electrolyte according to the first aspect of the present disclosure, a content of the sulfonic ester cyclic quaternary ammonium salt is 0.05%~10% of a total mass of the electrolyte, a content of the multinitrile compound is 0.05%~7% of the total mass of the electrolyte. In the electrolyte of the present disclosure, under the combined effect of the sulfonic ester cyclic quaternary ammonium salt and the multinitrile compound, the high temperature cycle performance and the high temperature storage performance of the electrochemical energy storage device can be improved, it should be noted that, changes of the contents the sulfonic ester cyclic quaternary ammonium salt and the multinitrile compound will directly influence performance of the electrolyte, so as to influence the improvement of electrochemical performance of the electrochemical energy storage device. For example, if the content of the sulfonic ester cyclic quaternary ammonium salt and/or the content of the multinitrile compound are/is too low, the SEI film formed is too thin to prevent continuous oxidation reaction and reduction reaction of the electrolyte from occurring on the surface of the positive, negative electrode films, therefore the improvement of electrochemical performance of the electrochemical energy storage device is not obvious, particularly the improvement of the high temperature storage performance is not obvious. If the content of the sulfonic ester cyclic quaternary ammonium salt and/or the content of the multinitrile compound are/is too high, interface impedances of the positive, negative electrode films will be increased to a certain extent, which is not beneficial to improve performance of the electrochemical energy storage device. But for some non-high requirements of use, as long as the sulfonic ester cyclic quaternary ammonium salt and the multinitrile compound are added into the electrolyte at the same time, the high temperature cycle performance and the high temperature storage performance of the electrochemical energy storage device can be improved to a certain extent. Preferably, the content of the sulfonic ester cyclic quaternary ammonium salt is 0.1%~5% of the total mass of the electrolyte, the content of the multinitrile compound is 0.1%~4% of the total mass of the electrolyte.

In the electrolyte according to the first aspect of the present disclosure, the electrolyte further comprises an organic solvent, a type of the organic solvent is not particularly limited and may be selected according to actual demand. Preferably, the organic solvent is non-aqueous organic solvent. The non-aqueous organic solvent may comprise any kind of carbonate and/or carboxylate. The carbonate may comprise cyclic carbonate ester or chain carbonate ester. The non-aqueous organic solvent may further comprise halogenated carbonate ester. Specifically, the organic solvent may be one or more selected from a group consisting of ethylene carbonate, propylene carbonate, butylene carbonate, pentylene carbonate, fluoroethylene carbonate, dimethyl carbonate, diethyl carbonate, dipropyl carbonate, ethyl methyl carbonate, methyl formate, ethyl formate, ethyl acetate, propyl propionate, ethyl propionate, γ-butyrolactone and tetrahydrofuran.

In the electrolyte according to the first aspect of the present disclosure, a content of the electrolyte salt is not specifically limited and may be selected according to actual demand. Specifically, the content of the electrolyte salt is 6%~25% of the total mass of the electrolyte, preferably, the content of the electrolyte salt is 6%~20% of the total mass of the electrolyte, further preferably, the content of the electrolyte salt is 10%~15% of the total mass of the electrolyte.

Next an electrochemical energy storage device according to a second aspect of the present disclosure is described.

The electrochemical energy storage device according to a second aspect of the present disclosure comprises the electrolyte according to the first aspect of the present disclosure.

In the electrochemical energy storage device according to the second aspect of the present disclosure, the electrochemical energy storage device further comprises a positive electrode plate, a negative electrode plate, a separator and a package case.

In the electrochemical energy storage device according to the second aspect of the present disclosure, it should be noted that, the electrochemical energy storage device may be a lithium-ion battery, a sodium-ion battery, a zinc-ion battery, a lithium metal battery, a solid state lithium battery, a solid state sodium battery or a supercapacitor. In examples of the present disclosure, only a lithium-ion battery as the electrochemical energy storage device is described, but the present disclosure is not limited to this.

In the lithium-ion battery, the positive electrode plate comprises a positive electrode current collector and a positive electrode film provided on the positive electrode current collector. The positive electrode current collector is an aluminum foil. The positive electrode film comprises a positive electrode active material, the positive electrode film may further comprise a conductive agent and a binder. The positive electrode active material may be selected from a group consisting of lithium cobalt oxide ($LiCoO_2$), lithium nickel oxide ($LiNiO_2$), spinel-type lithium manganese dioxide ($LiMn_2O_4$), olivine-type $LiMPO_4$ and $Li_aNi_xA_yB_{(1-x-y)}O_2$. Here, in the olivine-type $LiMPO_4$, M is one or more selected from a group consisting of Co, Ni, Fe, Mn and V; in the $Li_aNi_xA_yB_{(1-x-y)}O_2$, A and B each independently are one selected from a group consisting of Co, Al and Mn, and A and B is different, $0.95 \leq a \leq 1.2$, $0<x<1$, $0<y<1$, and $x+y<1$. A type of the conductive agent and the binder is not particularly limited and may be selected according to actual demand.

In the lithium-ion battery, the negative electrode plate comprises a negative electrode current collector and a negative electrode film provided on the negative electrode current collector. The negative electrode current collector is a copper foil. The negative electrode film comprises a negative electrode active material, the negative electrode film may further comprise a conductive agent and a binder. The negative electrode active material may be selected from materials that lithium-ion can be intercalated under voltage less than 2V (vs. $Li/Li^+$). Specifically, the negative electrode active material may be one or more selected from a group consisting of natural graphite, artificial graphite, mesocarbon microbead (abbreviated as MCMB), hard carbon, soft carbon, silicon, silicon-carbon composite, Li—Sn alloy, Li—Sn—O alloy, Sn, SnO, $SnO_2$, spinel-type lithiation $TiO_2$—$Li_4Ti_5O_{12}$ and Li—Al alloy. A type of the conductive agent and the binder is not particularly limited and may be selected according to actual demand. The negative electrode plate can also directly use a lithium metal plate.

In the lithium-ion battery, the electrolyte salt may be a lithium salt, a specific type of the lithium salt is not limited. Preferably, the lithium salt at least comprises $LiPF_6$. The lithium salt may further comprise one or more selected from a group consisting of $LiBF_4$, LiFSI, LiTFSI, $LiClO_4$, $LiAsF_6$, LiBOB, LiDFOB, $LiPO_2F_2$, LiTFOP, $LiN(SO_2RF)_2$, $LiN(SO_2F)(SO_2RF)$, where, $RF=\!\!=\!\!-CnF_{2n+1}$, that is RF represents saturated perfluoroalkyl group, n is an integer of 1~10.

In the lithium-ion battery, a type of the separator is not particularly limited and may be selected according to actual demand, specifically, the separator may be selected from a polyethylene film, a polypropylene film, a polyvinylidene fluoride film and a multilayer composite films thereof.

Hereinafter the present disclosure will be described in detail in combination with examples. It should be noted that, the examples described in the present disclosure are only used for explaining the present disclosure, and are not intended to limit the present disclosure. In the examples, only a lithium-ion battery as the electrochemical energy storage device is described, but the present disclosure is not limited to this.

In the following example, the reagents, materials and instruments used are commercially available unless otherwise specified. The sulfonic ester cyclic quaternary ammonium salt used may refer to Chinese patent application publication No. CN105845981A published on Aug. 10, 2016.

The lithium-ion batteries of examples 1~13 and comparative examples 1~7 were all prepared as follows:

(1) Preparation of a positive electrode plate: $LiNi_{0.6}Co_{0.2}Mn_{0.2}O_2$ (positive electrode active material), acetylene black (conductive agent), polyvinylidene fluoride (binder) according to a mass ratio of 98:1:1 were mixed with N-methyl-2-pyrrolidone (solvent) under vacuum mixer to form a uniform and transparent positive electrode slurry; then the positive electrode slurry was uniformly coated on an aluminum foil (positive electrode current collector) with a thickness of 12 μm; drying under room temperature was then performed, which was followed by moving the aluminum foil to an oven for baking 1 h under 120° C., then after cold-pressing and slitting, the positive electrode plate was obtained.

(2) Preparation of a negative electrode plate: artificial graphite (negative electrode active material), sodium carboxymethylcellulose (thickening agent, CMC), styrene butadiene rubber (binder) according to a mass ratio of 98:1:1 were mixed with deionized water under vacuum mixer to form a negative electrode slurry; then the negative electrode slurry was uniformly coated on a copper foil (negative electrode current collector) with a thickness of 8 μm; drying under room temperature was then performed, which was followed by moving the copper foil to an oven for baking 1 h under 120° C., then after cold-pressing and slitting, the negative electrode plate was obtained.

(3) Preparation of an electrolyte: in an argon atmosphere glove box in which the water content was less than 10 ppm, ethylene carbonate (EC), propylene carbonate (PC), diethyl carbonate (DEC) according to a volume ratio of EC:PC:DEC=1:1:1 were mixed as a mixed organic solvent, then fully dried lithium salt $LiPF_6$ was dissolved into the mixed organic solvent, next the sulfonic ester cyclic quaternary ammonium salt and the multinitrile compound were added, after uniformly mixing, the electrolyte was obtained. Where, a content of $LiPF_6$ was 12.5% of the total mass of the electrolyte. The types and the contents of the sulfonic ester cyclic quaternary ammonium salt and the multinitrile compound of the electrolyte were shown in table 1, and in the table 1, the content of the sulfonic ester cyclic quaternary ammonium salt and the content of the multinitrile compound were mass percent based on the total mass of the electrolyte.

(4) Preparation of a separator: a polypropylene separator with a thickness of 16 μm (model A273, provided by Celgard Company) was used as the separator.

(5) Preparation of a lithium-ion battery: the positive electrode plate, the separator, the negative electrode plate were laminated in order so as to make the separator positioned between the positive electrode plate and the negative electrode plate and separate the positive electrode plate and the negative electrode plate, then were wound to form an electrode assembly and placed in a package case, next the prepared electrolyte was injected into the dried electrode assembly, after vacuum packaging, standing-by, forming, shaping and the like, the lithium-ion battery was obtained.

TABLE 1

Parameters of examples 1~13 and comparative examples 1~7

| | Sulfonic ester cyclic quaternary ammonium salt | | Multinitrile compound | |
|---|---|---|---|---|
| | Type | Content/% | Type | Content/% |
| Example 1 | Compound 1 | 0.05 | 1,2-bis(2-cyanoethoxy)ethane | 1 |
| Example 2 | Compound 1 | 0.1 | 1,2-bis(2-cyanoethoxy)ethane | 1 |
| Example 3 | Compound 1 | 1 | 1,2-bis(2-cyanoethoxy)ethane | 1 |
| Example 4 | Compound 1 | 5 | 1,2-bis(2-cyanoethoxy)ethane | 1 |
| Example 5 | Compound 1 | 10 | 1,2-bis(2-cyanoethoxy)ethane | 1 |
| Example 6 | Compound 1 | 1 | 1,2-bis(2-cyanoethoxy)ethane | 0.05 |
| Example 7 | Compound 1 | 1 | 1,2-bis(2-cyanoethoxy)ethane | 0.1 |
| Example 8 | Compound 1 | 1 | 1,2-bis(2-cyanoethoxy)ethane | 3 |
| Example 9 | Compound 1 | 1 | 1,2-bis(2-cyanoethoxy)ethane | 4 |
| Example 10 | Compound 1 | 1 | 1,2-bis(2-cyanoethoxy)ethane | 7 |
| Example 11 | Compound 3 | 1 | 1,2-bis(2-cyanoethoxy)ethane | 1 |
| Example 12 | Compound 5 | 1 | 1,3,6-hexanetricarbonitrile | 1 |
| Example 13 | Compound 6 | 1 | tetracyanoethylene | 1 |
| Comparative example 1 | — | — | — | — |
| Comparative example 2 | Compound 1 | 1 | — | — |
| Comparative example 3 | — | — | 1,2-bis(2-cyanoethoxy)ethane | 1 |
| Comparative example 4 | Compound 1 | 0.03 | 1,2-bis(2-cyanoethoxy)ethane | 1 |
| Comparative example 5 | Compound 1 | 11 | 1,2-bis(2-cyanoethoxy)ethane | 1 |
| Comparative example 6 | Compound 1 | 1 | 1,2-bis(2-cyanoethoxy)ethane | 0.03 |
| Comparative example 7 | Compound 1 | 1 | 1,2-bis(2-cyanoethoxy)ethane | 8 |

Finally, test processes and test results of the lithium-ion batteries were described.

(1) Lithium-ion Battery High Temperature Cycle Performance

At 45° C., the lithium-ion battery was charged to a voltage of 4.4V at a constant current of 1 C, further the lithium-ion battery was charged to a current of 0.05 C at a constant voltage of 4.4V, then the lithium-ion battery was discharged to a voltage of 3.0V at a constant current of 1 C, this was a charge-discharge cycle process, discharged capacity this time was marked as discharge capacity of the first cycle. Then the charge-discharge cycle of the lithium-ion battery was performed as above, discharged capacity of $300^{th}$ cycle was marked. Fifteen lithium-ion batteries were tested in each group to take an average value.

Capacity retention rate after $300^{th}$ cycle under 45° C. of the lithium-ion battery (%)=(discharged capacity of $300^{th}$ cycle of the lithium-ion battery/discharged capacity of the first cycle of the lithium-ion battery)×100%.

(2) Test of High Temperature Storage Performance of the Lithium-Ion Battery

At 25° C., the lithium-ion battery was charged to a voltage of 4.4V at a constant current of 0.5 C, then the lithium-ion battery was charged to a current of 0.05 C at a constant voltage of 4.4V, a thickness of the lithium-ion battery this time was tested and marked as h0; next the lithium-ion battery was stored in a thermostat for 30 days under 60° C., and then the lithium-ion battery was taken out, a thickness of the lithium-ion battery this time was tested and marked as h1. Fifteen lithium-ion batteries were test in each group to take an average value.

Thickness expansion rate after stored for 30 days under 60° C. of the lithium-ion battery (%)= [($h1-h0$)/$h0$]×100%.

TABLE 2

Test results of examples 1~13 and comparative examples 1~7

| | Thickness expansion rate after stored for 30 days under 60° C. | Capacity retention rate after $300^{th}$ cycle under 45° C. |
|---|---|---|
| Example 1 | 14.50% | 64.50% |
| Example 2 | 13.41% | 66.17% |
| Example 3 | 11.95% | 70.98% |
| Example 4 | 10.80% | 74.90% |
| Example 5 | 10.10% | 64.72% |
| Example 6 | 37.00% | 70.15% |
| Example 7 | 26.79% | 70.43% |
| Example 8 | 5.92% | 67.10% |
| Example 9 | 5.60% | 66.81% |
| Example 10 | 4.21% | 64.72% |
| Example 11 | 12.78% | 69.88% |
| Example 12 | 9.87% | 71.36% |
| Example 13 | 9.95% | 71.06% |
| Comparative example 1 | 42.50% | 63.70% |
| Comparative example 2 | 38.70% | 70.10% |
| Comparative example 3 | 15.10% | 64.10% |
| Comparative example 4 | 15.00% | 64.30% |
| Comparative example 5 | 6.10% | 61.40% |
| Comparative example 6 | 37.02% | 70.12% |
| Comparative example 7 | 4.20% | 59.98% |

It could be seen from table 2, the lithium-ion battery had excellent high temperature storage performance and high temperature cycle performance under the combined effect of the sulfonic ester cyclic quaternary ammonium salt and the multinitrile compound.

In comparative examples 1~3, the sulfonic ester cyclic quaternary ammonium salt and the multinitrile compound were not added into the electrolyte of comparative example 1, capacity retention rate after $300^{th}$ cycle under 45° C. was lower but thickness expansion rate after stored for 30 days under 60° C. of the lithium-ion battery was higher; the sulfonic ester cyclic quaternary ammonium salt was added into the electrolyte of comparative example 2, capacity retention rate after $300^{th}$ cycle under 45° C. and thickness expansion rate after stored for 30 days under 60° C. of the lithium-ion battery were both improved to a certain extent, where, improvement of capacity retention rate after $300^{th}$ cycle under 45° C. of lithium-ion battery was more obvious, but improvement of thickness expansion rate after stored for 30 days under 60° C. was not obvious, therefore the lithium-ion battery of the comparative example 2 could not meet actual usage requirements; the multinitrile compound was added into the electrolyte of comparative example 3, thickness expansion rate after stored for 30 days under 60° C. of the lithium-ion battery was obviously improved, but improvement of capacity retention rate after $300^{th}$ cycle under 45° C. of the lithium-ion battery was not obvious.

In examples 1~13 and comparative examples 4~7, the sulfonic ester cyclic quaternary ammonium salt and the multinitrile compound were added into the electrolyte at the same time, the lithium-ion battery had excellent high temperature storage performance and high temperature cycle performance, it should be noted that at the same time, changes of the contents of the sulfonic ester cyclic quaternary ammonium salt and the multinitrile compound would directly influence performance of the electrolyte, and in turn influence improvements of performance of the lithium-ion battery electrochemical performance.

In comparative example 4, the content of the sulfonic ester cyclic quaternary ammonium salt was insufficient, improvement of high temperature cycle performance of the lithium-ion battery was weakened. In examples 1~5, as the content of the sulfonic ester cyclic quaternary ammonium salt increased, thickness expansion rate after stored for 30 days under 60° C. of the lithium-ion battery could be obviously decreased, and capacity retention rate after $300^{th}$ cycle under 45° C. of the lithium-ion battery could be improved to a certain extent at the same time. When the content of the sulfonic ester cyclic quaternary ammonium salt was too high, for example in comparative example 5, high temperature cycle performance of the lithium-ion battery could be obviously deteriorated.

In comparative example 6, the content of the multinitrile compound was insufficient, improvement of high temperature storage performance of the lithium-ion battery was not obvious. In examples 6~10, as the content of the multinitrile compound content increased, capacity retention rate after $300^{th}$ cycle under 45° C. of the lithium-ion battery could be generally stable, thickness expansion rate after stored for 30 days under 60° C. of the lithium-ion battery could be improved obviously. However when the content of the multinitrile compound was too high, for example in comparative example 7, high temperature cycle performance of the lithium-ion battery could be obviously deteriorated.

Therefore too low content or too high content of each of the sulfonic ester cyclic quaternary ammonium salt and the multinitrile compound were both not beneficial to improve electrochemical performance of the lithium-ion battery, but for some non-high requirements, they could also improve electrochemical performance of the lithium-ion battery to a certain extent.

According to the revelations of the present disclosure, a person skilled in the art may also make appropriate variations and modifications to the above embodiments. Therefore, the present disclosure is not limited to the specific embodiments disclosed and described as above, modifications and variations of the present disclosure will also be fallen within the scope of the appended claims of the present disclosure.

What is claimed:

1. An electrolyte, comprising:
an electrolyte salt; and
an additive;
wherein the additive comprises a sulfonic ester cyclic quaternary ammonium salt and a multinitrile compound;
wherein the sulfonic ester cyclic quaternary ammonium salt is

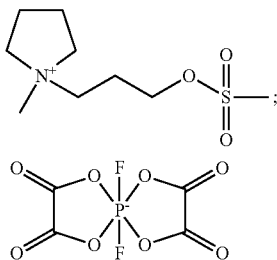

the multinitrile compound is ethylene glycol bis(propionitrile) ether;
a content of the sulfonic ester cyclic quaternary ammonium salt is 0.05%~10% of a total mass of the electrolyte; and
a content of the multinitrile compound is 0.05%~7% of the total mass of the electrolyte.

2. The electrolyte according to claim 1, wherein
the content of the sulfonic ester cyclic quaternary ammonium salt is 0.1%~5% of the total mass of the electrolyte; and
the content of the multinitrile compound is 0.1%~4% of the total mass of the electrolyte.

3. The electrolyte according to claim 1, wherein the electrolyte is a liquid electrolyte, a solid polymer electrolyte or a gel polymer electrolyte.

4. An electrochemical energy storage device, comprising an electrolyte;
the electrolyte comprising an electrolyte salt and an additive;
wherein the additive comprises a sulfonic ester cyclic quaternary ammonium salt and a multinitrile compound;
wherein the sulfonic ester cyclic quaternary ammonium salt is

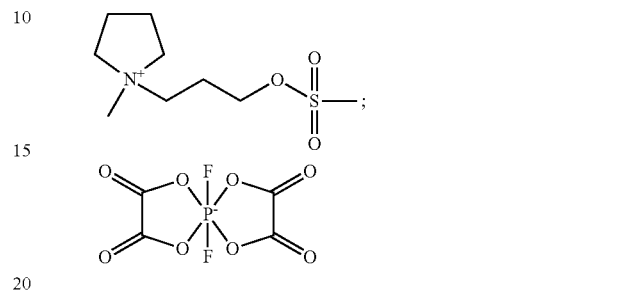

the multinitrile compound is ethylene glycol bis(propionitrile) ether;
a content of the sulfonic ester cyclic quaternary ammonium salt is 0.05%~10% of a total mass of the electrolyte; and
a content of the multinitrile compound is 0.05%~7% of the total mass of the electrolyte.

5. The electrochemical energy storage device according to claim 4, wherein
the content of the sulfonic ester cyclic quaternary ammonium salt is 0.1%~5% of the total mass of the electrolyte; and
the content of the multinitrile compound is 0.1%~4% of the total mass of the electrolyte.

6. The electrochemical energy storage device according to claim 4, wherein the electrolyte is a liquid electrolyte, a solid polymer electrolyte or a gel polymer electrolyte.

* * * * *